United States Patent [19]

Hofmann

[11] Patent Number: Plant 5,313

[45] Date of Patent: Oct. 30, 1984

[54] VARIETY OF GERANIUM NAMED 'LACHSBALL'

[75] Inventor: Guenter Hofmann, Dresden, German Democratic Rep.

[73] Assignee: Oglevee Associates, Inc., Connellsville, Pa.

[21] Appl. No.: 477,965

[22] Filed: Mar. 23, 1983

[51] Int. Cl.[3] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Robinson & Webb

[57] ABSTRACT

A new geranium cultivar is distinguished by its soft, pinkish-salmon color, short and compact plant, more basil branching, close internodes, smaller and lighter colored leaves with the flowers positioned closer to the foliage. In addition, early flowering is a distinguishing characteristic.

3 Drawing Figures

BACKGROUND OF THE NEW PLANT

The present invention comprises a new and distinct cultivar of *Pelargonium hortorum,* Bailey known by the varietal name of Lachsball. The new variety was discovered in a selective breeding program and is a seedling resulting from the cross of the seed parent Rubin and the pollen parent Adonis×Hannchen Ander.

The new cultivar was discovered in the year 1980 in Dresden, German Democratic Republic; was first asexually reproduced by cuttings in Dresden, German Democratic Republic and has been repeatedly asexually reproduced by cuttings at Oglevee Floral Company in Connellsville, Pa. over an eighteen month period. It has been trialed and field tested at Connellsville during the summers of 1981 and 1982. It has been found to retain its distinctive characteristics through successive propagation.

The new cultivar, when grown in a greenhouse in Connellsville, Pa., using natural light and 62° F. night temperature and 70° F. day temperature, has a response time of five weeks from a well rooted cutting to a flowering plant in a four inch (10 cms.) pot.

DESCRIPTION OF THE DRAWING

FIG. 1 is a graph of the flavonols fingerprinting.

DESCRIPTION OF THE NEW PLANT

Figure 1:
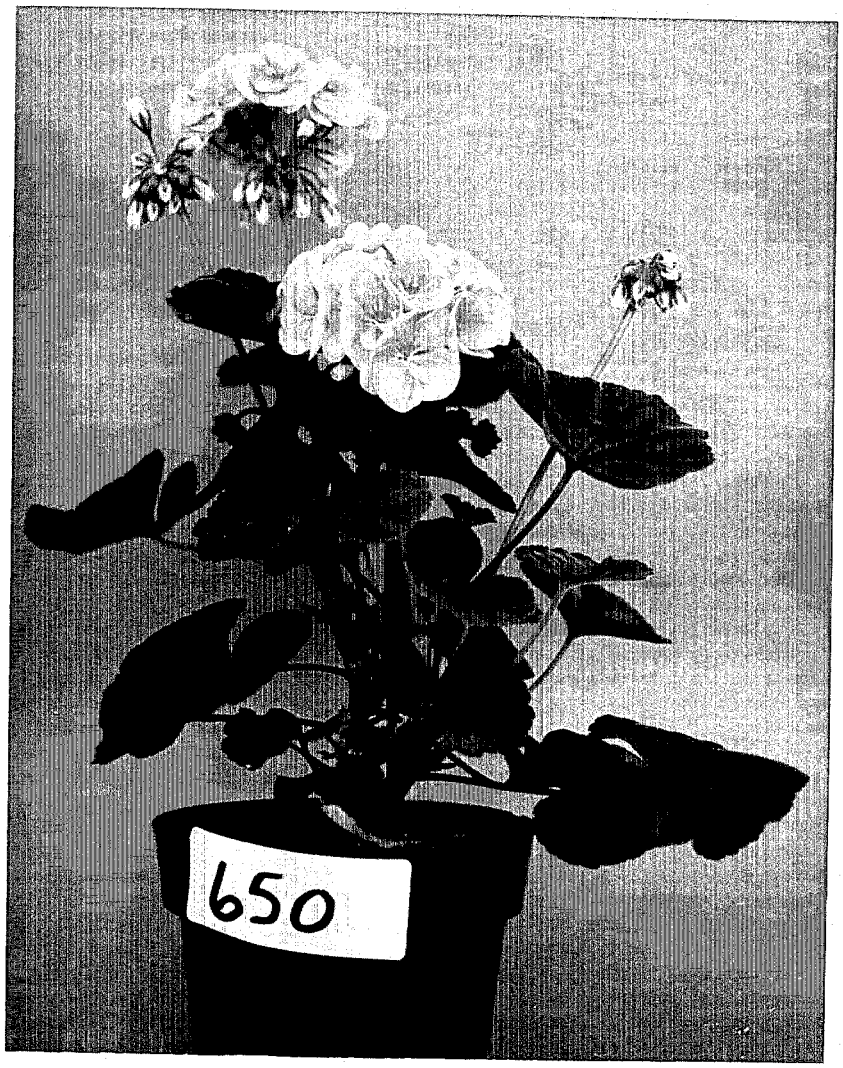
FIG. 1 of the accompanying photographic drawing illustrates the new cultivar, the color being as nearly true as possible with color illustrations of this type.

The following detailed descriptions set forth the characteristics of the new cultivar. The data which define these characteristics were collected from asexual reproductions carried out by the Oglevee Floral Company in Connellsville, Pa. The plant history was taken on five weeks plants, blossomed under natural light in a greenhouse and color readings were taken indoors under 100 foot candles of cool, white fluorescent light. Color references are primarily to the R.H.S. Colour Chart of The Royal Horticultural Society of London.

THE PLANT

Classification:

*Botanical.*—*Pelargonium hortorum,* Bailey.

*Commercial.*—Zonal geranium.

Form: Bush

Height: 12 to 18 cms. (15 cms. average) as a four inch pot plant excluding bloom and 22 to 28 cms. (25 cms. average) as a four inch pot plant including bloom.

Growth: Short and compact with more basil branching, closer internodes and smaller leaves as compared with commonly grown zonal geraniums.

Strength: Very sturdy with a low susceptibility to wind and rain damage.

Foliage: The quantity of foliage is average.

Leaves:

*Size.*—8 To 10.5 cms. across.

*Shape.*—Reniform with oblique base.

*Margin.*—Cuneate.

*Texture.*—Leathery and pubescent.

*Color.*—Upperside — Fan 3 Green Group 137C. Underside — Fan 3 Green Group 138B.

*Ribs and veins.*—Palmate.

Petioles: 6 to 8 cms.

Stem:

*Color.*—Fan 1 Yellow Green Group 138A.

*Internodes.*—1 To 3 cms.

THE BUD

Shape: Umbel formed with 50 florets.

Size: As bud develops at first color show, head size is 2.5 cms. and it opens into a fully developed head size of 10 cms.

INFLORESCENCE

Blooming habit: Continuous throughout the year.

Size: Approximately 10 cms.

Borne: Singly in an umbel form.

Florets:

*Form.*—Slightly cupped.

*Petals.*—5 To 6 petals, plus 1 to 3 petaloids.

*Upperside.*—Throat area (barely visible) is white. Throat blends into Fan 1 Red Group 38A, which is the predominant color at a distance. Edge area is off-white Fan 1 Red Group 49D. Pencilling occurs throughout petal and is Fan 1 Red Group 49A.

*Underside.*—Blend of three colors, namely Fan 1 Red Group 49C, Fan 1 Red Group 49B and Fan 1 Red Group 56C.

*Texture and appearance.*—Firm and satiny.

*Size.*—5 cms.

Petaloids:

*Quantity.*—1 To 3 in number.

*Shape.*—Small and twisted.

*Color.*—Same as florets.

Pedicel:

*Length.*—2.5 To 3 cms.

Peduncle:

*Length.*—16 To 18 cms.

Persistance: Nonshattering.

Disease resistance: Excellent.

Lasting quality: Three weeks.

REPRODUCTIVE ORGANS

Stamens:

*Anthers.*—5 To 7 in number, imperfectly formed.

*Filaments.*—Stuck together in cup shape; flattened, 8 to 10 in number, 6 to 8 mms. in length, white with reddish purple tips.

*Pollen.*—Reddish brown.

Pistils:

*Number.*—1.

*Length.*—8 mms.

*Stigma.*—5 Arms, reflexed, reddish in color.

*Style.*—Reddish in color.

Ovaries: Green, 5 carpels.

Fruit: Nonfertile.

The following evaluation is a result of the trialing and field testing carried out in the summer of 1982 at Connellsville, Pa. and compares the new geranium cultivar to the standard cultivar "Penny" presently commercialized in the United States. The ratings are taken on plants planted in June and evaluated as to height, flowering, number of flowers, heat tolerance and form. The rating is based on a weighted average. A rating of 1.0 is poor and a rating of 10.0 is outstanding.

| | EVALUATIONS | | | AVERAGE SEASONAL |
|---|---|---|---|---|
| CULTIVARS | 7/13/82 | 8/15/82 | 9/15/82 | RATING |
| LACHSBALL | 7.5 | 9.0 | 9.0 | 8.5 |
| PENNY | 7.0 | 7.0 | 7.0 | 7.0 |

The new cultivar is characterized by its soft, pinkish-salmon color and its short and compact plant. There is more basil branching, close internodes and smaller and lighter colored leaves as compared with the standard bush zonal geraniums produced in the United States. Flowers are positioned closer to the foliage thereby rendering the plants very resistant to wind and rain damage. The cultivar is further characterized by its early flowering and its excellent disease resistance.

Figure 2:
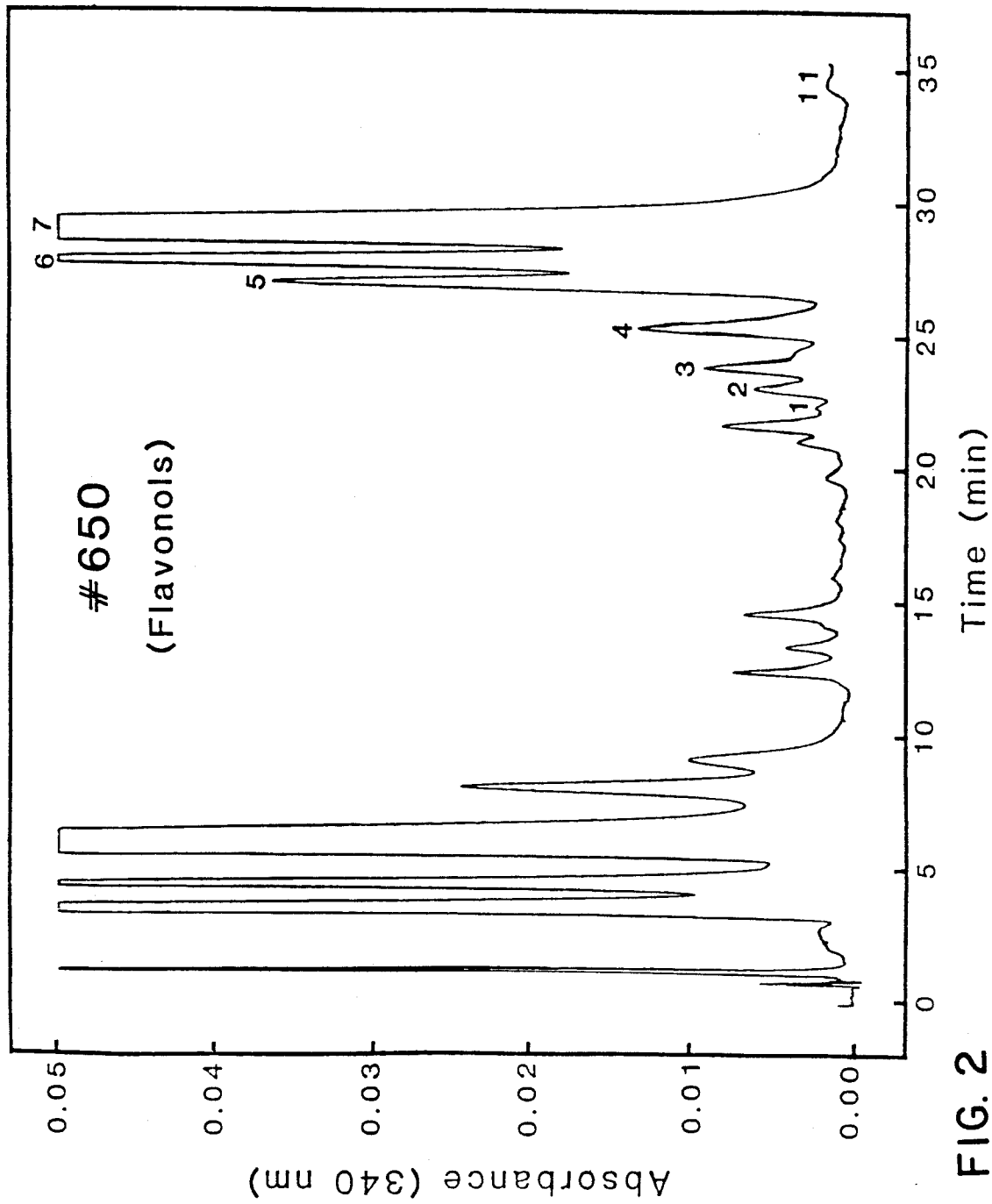
FIG. 2 is a graph of flavonols fingerprinting.
Figure 3:
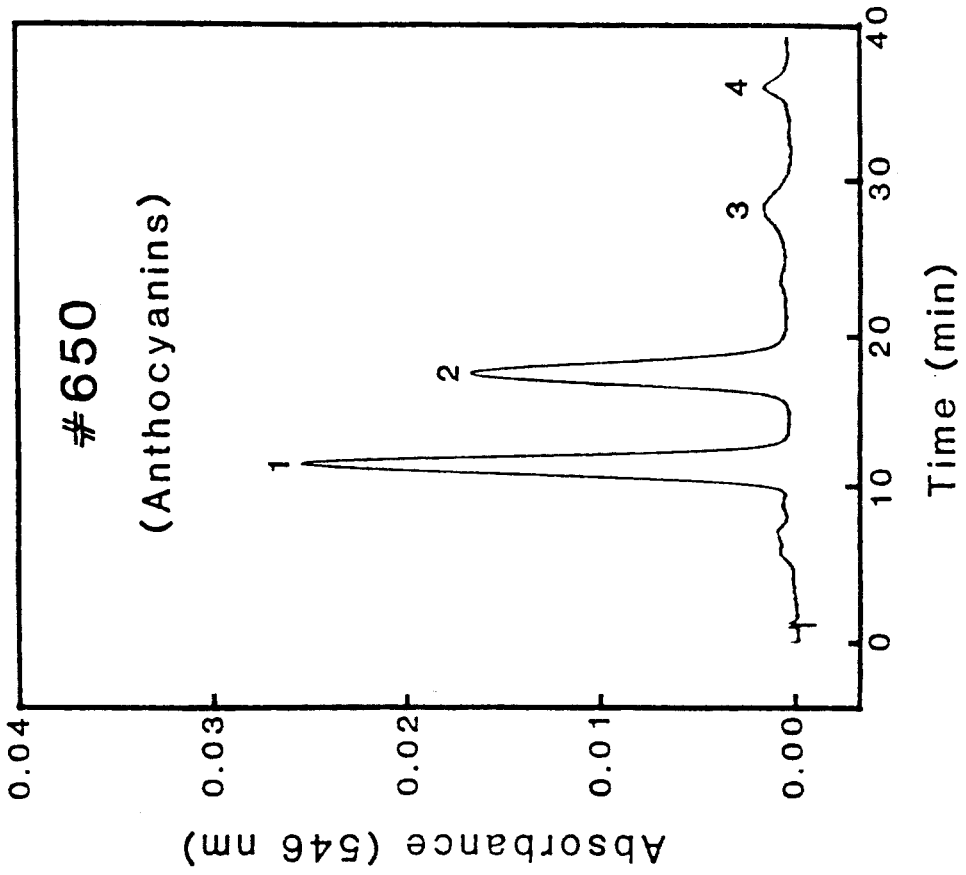
FIG. 3 is a graph of the anthocyanins fingerprinting of the new cultivar.

The new cultivar has been fingerprinted by the U.S. Department of Agriculture, Florist and Nursery Crops Laboratory, Beltsville, Md. Young plants arrived from Oglevee Floral Company of Connelsville, Pa. and were grown under standard conditions in a greenhouse at Beltsville, Md. The fingerprinting was conducted by high pressure liquid chromatographic analysis of the anthocyanin and flavonol chemical markers utilizing flower petals as an adjunct for cultivar identification. Petals were selected for analysis from individual mature flowers sampled just after anthesis. It should be noted that changes in environment can influence the biosynthesis of the flavonoids. The absorption profiles (fingerprints) are illustrated in FIGS. 2 and 3.

I claim:

1. A new and distinct variety of geranium plant substantially as herein shown and described.

* * * * *

UNITED STATES PATENT AND TRADEMARK OFFICE

CERTIFICATE OF CORRECTION

Plant
PATENT NO. : 5, 313

DATED : October 30, 1984

INVENTOR(S) : Guenter Hofmann

It is certified that error appears in the above-identified patent and that said Letters Patent is hereby corrected as shown below:

Column 1 Line 15 After "has" insert --also--.

Column 1 Line 30

Delete --FIG. 1 is a graph of the flavonols fingerprinting.--.

Signed and Sealed this

*Ninth* Day of *April 1985*

[SEAL]

*Attest:*

DONALD J. QUIGG

*Attesting Officer* *Acting Commissioner of Patents and Trademarks*